(12) United States Patent
Hemphill et al.

(10) Patent No.: US 9,852,849 B2
(45) Date of Patent: Dec. 26, 2017

(54) USING ETCH RESIST PATTERNS AND FORMATION FOR FACILITATION OF LASER CUTTING, PARTICLE AND LEAKAGE CURRENT REDUCTION

(71) Applicant: Pacesetter, Inc., Sunnyvale, CA (US)

(72) Inventors: Ralph Jason Hemphill, Sunset, SC (US); Thomas F. Strange, Easley, SC (US); David R. Bowen, Taylors, SC (US); Troy L. McCurry, West Union, SC (US); Peter Fernstrom, Easley, SC (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 15/167,474

(22) Filed: May 27, 2016

(65) Prior Publication Data
US 2017/0345580 A1    Nov. 30, 2017

(51) Int. Cl.
*H01G 9/00*        (2006.01)
*H01G 9/045*       (2006.01)
(Continued)

(52) U.S. Cl.
CPC .......... *H01G 9/0029* (2013.01); *A61N 1/025* (2013.01); *C23F 1/02* (2013.01); *C25F 3/14* (2013.01); *H01G 9/045* (2013.01); *H01G 9/145* (2013.01)

(58) Field of Classification Search
CPC ...... H01G 9/045; H01G 9/0029; H01G 9/145; H01G 9/055; A61N 1/025; C25F 3/00;
(Continued)

(56) References Cited

U.S. PATENT DOCUMENTS 3,779,877 A    12/1973  Alwitt
3,872,579 A     3/1975  Papadopoulous
(Continued)

FOREIGN PATENT DOCUMENTS

JP    59083772    5/1984
JP    02075155    3/1990
(Continued)

OTHER PUBLICATIONS

Non-Final Office Action dated Nov. 3, 2004; Related U.S. Appl. No. 10/680,777.
(Continued)

*Primary Examiner* — Scott B Geyer
(74) *Attorney, Agent, or Firm* — Theresa A. Raymer (57) ABSTRACT

A process for creating an anode foil for use in an electrolytic capacitor of an implantable cardioverter defibrillator is provided. The process includes placing a partially masked bulk metal foil in an etch electrolyte solution to etch exposed area of the bulk metal foil, removing the etch-resistant mask to expose the unetched areas, widening the bulk metal foil, and partially cutting the bulk metal foil between a plurality of unetched areas to form a partially detached etched foil anode, such that the unetched areas are not cut and the unetched areas serve as attachment tabs to keep the partially detached etched foil anode attached to the bulk metal foil. Additionally, the process may include an oxide formation step, wherein the step of partially cutting the bulk metal foil is performed after the etching and widening steps, and before the oxide formation step.

21 Claims, 10 Drawing Sheets

(51) Int. Cl.
*H01G 9/145* (2006.01)
*A61N 1/02* (2006.01)
*C23F 1/02* (2006.01)
*C25F 3/14* (2006.01)

(58) Field of Classification Search
CPC ...... C25F 3/02; C25F 3/04; C25F 3/14; C23F 1/02; C23F 4/04
See application file for complete search history.

(56) References Cited

U.S. PATENT DOCUMENTS

| | | | |
|---|---|---|---|
| 4,213,835 A | 7/1980 | Fickelscher | |
| 4,266,332 A | 5/1981 | Markarian et al. | |
| 4,420,367 A | 12/1983 | Locher | |
| 4,474,657 A | 10/1984 | Arora | |
| 4,481,084 A | 11/1984 | Chen et al. | |
| 4,518,471 A | 5/1985 | Arora | |
| 4,525,249 A | 6/1985 | Arora | |
| 4,541,037 A | 9/1985 | Ross et al. | |
| 4,593,343 A | 6/1986 | Ross | |
| 4,663,824 A | 5/1987 | Kenmochi | |
| 4,696,082 A | 9/1987 | Fonfia et al. | |
| 5,131,388 A | 7/1992 | Pless et al. | |
| 5,175,227 A | 12/1992 | Gardon et al. | |
| 5,230,962 A | 7/1993 | Stephenson | |
| 5,522,841 A | 6/1996 | Roby et al. | |
| 5,522,851 A | 6/1996 | Fayram | |
| 5,602,198 A | 2/1997 | Das et al. | |
| 5,660,737 A | 8/1997 | Elias et al. | |
| 5,663,240 A | 9/1997 | Simeone et al. | |
| 5,715,133 A | 2/1998 | Harrington et al. | |
| 6,168,706 B1 | 1/2001 | Hemphill et al. | |
| 6,224,738 B1 | 5/2001 | Sudduth et al. | |
| 6,426,864 B1 | 7/2002 | O'Phelan et al. | |
| 6,686,124 B1 | 2/2004 | Angelopoulos et al. | |
| 6,736,956 B1 | 5/2004 | Hemphill et al. | |
| 6,802,954 B1 | 10/2004 | Hemphill et al. | |
| 6,858,126 B1 | 2/2005 | Hemphill et al. | |
| 7,452,473 B1 | 11/2008 | Hemphill et al. | |
| 7,745,281 B2 | 6/2010 | Prymak et al. | |
| 8,535,507 B1 | 9/2013 | Hemphill et al. | |
| 8,734,964 B2 | 5/2014 | Kurihara et al. | |
| 8,888,967 B2 | 11/2014 | Hemphill et al. | |
| 9,275,800 B2 | 3/2016 | Ribble et al. | |
| 9,412,525 B2 | 8/2016 | Bowen et al. | |
| 2002/0111029 A1 | 8/2002 | Johnson | |
| 2017/0207030 A1* | 7/2017 | Strange | H01G 9/042 |

FOREIGN PATENT DOCUMENTS

| | | |
|---|---|---|
| JP | 04056309 | 2/1992 |
| JP | 07049428 | 2/1995 |
| WO | 00/19470 A1 | 4/2000 |

OTHER PUBLICATIONS

"A New Coating Process for Aluminum" by Patel et al. Posted on Oct. 25, 2000 on http://www.ceramicindustry.com, Downloaded from http://www.ceramicindustry.com/CDA/ArticleInformation/Features/BNP_Features_Item/0,270,13647,00.html on Oct. 21, 2004.
Amendment filed Mar. 3, 2005; Related U.S. Appl. No. 10/680,777.
Final Office Action dated May 23, 2005; Related U.S. Appl. No. 10/680,777.
Notice of Appeal mailed Sep. 23, 2005; Related U.S. Appl. No. 10/680,777.
Amendment filed Sep. 23, 2005; Related U.S. Appl. No. 10/680,777.
Notice of Allowance dated Sep. 24, 2008; Related U.S. Appl. No. 10/940,793.
Amendment filed Aug. 28, 2008; Related U.S. Appl. No. 10/940,793.
Examiner Interview Summary dated Aug. 1, 2008; Related U.S. Appl. No. 10/940,793.
Amendment filed Jun. 30, 2008; Related U.S. Appl. No. 10/940,793.
Final Office Action dated Mar. 28, 2008; Related U.S. Appl. No. 10/940,793.
Amendment filed Jan. 7, 2008; Related U.S. Appl. No. 10/940,793.
Non-Final Office Action dated Oct. 5, 2007; Related U.S. Appl. No. 10/940,793.
Amendment filed Sep. 21, 2007; Related U.S. Appl. No. 10/940,793.
Final Office Action dated Jun. 21, 2007; Related U.S. Appl. No. 10/940,793.
Amendment filed Apr. 10, 2007; Related U.S. Appl. No. 10/940,793.
Non-Final Office Action dated Jan. 10, 2007; Related U.S. Appl. No. 10/940,793.
English translation of JP 059-083772 performed by USPTO Translator Akiko Smith.

\* cited by examiner

USING ETCH RESIST PATTERNS AND FORMATION FOR FACILITATION OF LASER CUTTING, PARTICLE AND LEAKAGE CURRENT REDUCTION

BACKGROUND OF THE INVENTION

Field of the Invention

The present invention is directed to etching anodic foil to be used in electrolytic capacitors and more particularly, to a method of etching of anode foil to produce higher capacitance foil with improved leakage current and deformation, and to an electrolytic capacitor incorporating the etched anode foil of the present invention for use in an implantable cardioverter defibrillator (ICD).

Related Art

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators, such as those disclosed in U.S. Pat. No. 5,131,388, incorporated herein by reference, typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

Electrolytic capacitors are used in ICDs because they have the most nearly ideal properties in terms of size, reliability and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is the preferred metal for the anode plates, other metals such as tantalum, magnesium, titanium, niobium, zirconium and zinc may be used. A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent. The entire laminate is rolled up into the form of a substantially cylindrical body, or wound roll, that is held together with adhesive tape and is encased, with the aid of suitable insulation, in an aluminum tube or canister. Connections to the anode and the cathode are made via tabs. Alternative flat constructions for aluminum electrolytic capacitors are also known, comprising a planar, layered, stack structure of electrode materials with separators interposed therebetween, such as those disclosed in the above-mentioned U.S. Pat. No. 5,131,388.

In ICDs, as in other applications where space is a critical design element, it is desirable to use capacitors with the greatest possible capacitance per unit volume. Since the capacitance of an electrolytic capacitor increases with the surface area of its electrodes, increasing the surface area of the anode foil results in increased capacitance per unit volume of the electrolytic capacitor. By electrolytically etching an anode foil, an enlargement of a surface area of the foil will occur. Electrolytic capacitors which are manufactured with such etched foils can obtain a given capacity with a smaller volume than an electrolytic capacitor which utilizes a foil with an unetched surface.

In a conventional electrolytic etching process, surface area of the foil is increased by electrochemically removing portions of the foil to create etch tunnels. For example, U.S. Pat. Nos. 4,474,657, 4,518,471 and 4,525,249 to Arora disclose the etching of aluminum electrolytic capacitor foil by passing the foil through an electrolyte bath. The preferred bath contains 3% hydrochloric acid and 1% aluminum as aluminum chloride. The etching is carried out under a direct current (DC) and at a temperature of 75° C. U.S. Pat. No. 4,474,657 is limited to the above single step. U.S. Pat. No. 4,518,471 adds a second step where the etched foil is treated in a similar bath with a lower current density and at a temperature of 80-82.5° C. U.S. Pat. No. 4,525,249 adds a different second step, where the etched foil is treated in a bath of 8% nitric acid and 2.6% aluminum as a nitrate, at a temperature of 85° C.

The ideal etching structure is a pure tunnel-like etch with defined and uniform tunnel diameters and without any undesirable pitting of the foil. As tunnel density (i.e., the number of tunnels per square centimeter) is increased, a corresponding enlargement of the overall surface area will occur. Larger surface area results in higher overall capacitance. However, as tunnel density increases more of the aluminum foil is removed, reducing the strength of the remaining foil. Therefore a compromise must be made between foil strength and capacitance gain.

Traditionally, electrolytic capacitor foil is etched uniformly over the surface. With a uniform, random tunnel etch, the useable capacitance gain of the anode foil is limited by the strength requirements of the foil in its particular application. Thus, there is a need in the art for an etch process which increases the overall capacitance of the foil while retaining foil strength.

U.S. Pat. No. 5,660,737 to Elias et al. discloses a process providing an etch mask to cover during the etch process those portions of the anode foil which will be subjected to stress during the construction of the capacitor.

U.S. Pat. No. 6,736,956 to Hemphill et al. ("the Hemphill patent") discloses applying a mechanical grid to an etched foil to protect regions of the foil from further etching. The process of the Hemphill patent results in a web of lightly etched or unetched anode foil surrounding areas of more highly etched anode foil.

SUMMARY OF THE INVENTION

One aspect of the present invention is directed to a method of etching anode foil in a non-uniform manner which increases the overall capacitance of the foil while retaining foil strength. Non-etched tab connection areas are created around the edge of the anode by applying an etch-resist mask before the etching process. Masking the foil enables the succeeding steps of the method, which improves leakage current and deformation, eliminates friable edge, reduces conversion of boehmite aluminum oxide to alpha phase corundum, and retains foil strength.

In particular, by using a mask to protect regions of the foil from etching, a foil can be etched prior to a widening step. The higher surface area in the exposed areas does not significantly decrease the strength of the foil as a whole.

In one embodiment, an etch-resistant mask is applied to an aluminum anode foil prior to etching of the foil. The mask defines tab connection areas around the edge of the anode that are protected from etching while unmasked areas are exposed for etching. The mask may be applied by inkjet printing, lithography, photolithography, or other suitable means. The mask itself can be an acrylic ink, poly(4-hydroxystyrene), copolymers of 4-hydroxystyrene, novolac resins, fluorocarbon polymers, cycloaliphatic polymers, polyurethane polyols, polyesterurethanes, and cross-linked variants and copolymers and mixtures and thereof. Next, the foil is placed in an etch electrolyte solution and etched. The mask is applied in such a way that the etched/exposed area does not create large scale strength defects such as perforation holes and can be applied in any shape desired, such that the exposed area perimeter can be round, square, hexagonal, triangular, or any other shape and size. The mask is removed, and the foil is subject to widening and formation. The foil is then partially cut between the tabs, such that the unetched tabs are not cut and the partially detached etched foil anode remains attached to the bulk metal foil. After hydration or cleaning, the foil can then be formed before being completely cut. The partial cutting step enables formation of over 80% of the edge before complete cutting. The use of laser cutting and etch-resist masking are combined strategically to create patterns to prevent the anodes from becoming detached during formation.

A foil etched according to the present invention is suitable for use as an anode in an electrolytic capacitor. The cut anode foil will have minimized alpha-phase boehmite oxide corundum and enhanced capacitance without increased brittleness, which could render the foil unusable or suboptimal. Additional aspects of the invention are directed to such anodes and electrolytic capacitors.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

One aspect of the invention is directed to a process for etching an aluminum foil to minimize thermal oxidation and produce higher capacitance foil without sacrificing foil strength, to a process for creating an aluminum anode foil, and to an etched aluminum anode foil etched by such processes for use in an implantable cardioverter defibrillator (ICD).

Embodiments of the invention are now described. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

According to the present invention, an anode metal foil to be etched is selected. Aluminum foil is preferred, because of its ability to produce a sufficient quality oxide layer, its conductive properties, and its wide commercial availability. However, other foils conventionally utilized in electrolytic capacitors could also be used, including tantalum, magnesium, titanium, niobium, zirconium and zinc. Preferably, a 100 to 125 micron thick, unetched, high purity (at least 99.98%) strip of aluminum foil with high cubicity, wherein at least 80% the crystalline aluminum structure is oriented in a normal position (i.e., a (1,0,0) orientation) relative to the surface of the foil, is used. Such foils are well-known in the art and are readily available from commercial sources.

Initially, an etch-resistant mask is applied to a metal foil, such as aluminum foil. Application of the mask defines an unmasked or exposed area and a plurality of masked areas or tabs. Application of the mask protects the tabs from being etched and leaves the unmasked area exposed for etching. The resulting non-etched or unetched tabs allow for less oxide formation due to less surface area on the tabs along the edges of the anodes. Having less oxide improves the ability to cut through the aluminum foils, or to form etched anode foils with lower energy rates or lower heating. Additionally, the non-etched tabs allow for less surface area to form during the aging process, or less surface area to convert to alpha-phase oxide. In some embodiments, application of the mask also defines a perimeter or frame around the foil anode and connecting the masked tabs. Conversion of boehmite aluminum oxide to alpha-phase corundum has been found to cause the leakage current to increase by 100 to 200% and to increase deformation by at least 50 times. Reducing corundum formation allows laser cutting of anodes, which increases edge quality and productivity. Therefore, the leakage current will be reduced by the proportion of edge to anode surface. Additionally, the aging process will be faster leading to higher productivity. The tabs and frames can be created of various geometries to completely mask the tab or frame or create slight hazy tab or frame. The tab or frame can be applied to both sides or faces of the foil or only one side or face. A balance must be maintained by creating enough masking to laser cut the anode edge with tabs and not too much masking to reduce the anode capacitance significantly.

The etch-resistant mask may be applied by any suitable means known to persons of skill in the art. In some embodiments, the mask is applied using inkjet printing, lithography, or photolithography. Preferably, the mask is applied using inkjet printing. In some embodiments, the mask is cured optically without solvent. In some embodiments, the mask is cured using ultraviolet light.

The etch-resistant mask may be comprised of any suitable material or materials that resist etching in the etch electrolyte composition used. In some embodiments, the etch-resistant mask comprises an acrylic ink, poly(4-hydroxystyrene), copolymers of 4-hydroxystyrene, novolac resins, fluorocarbon polymers, cycloaliphatic polymers, polyurethane polyols, polyesterurethanes, and cross-linked variants and copolymers and mixtures and thereof. Preferably, the mask comprises an acrylic ink.

Next, the aluminum foil is placed in an etch electrolyte solution and etched, according to a conventional etch process, as known to those skilled in the relevant art, to produce an enlargement of surface area of at least 20 times. Reference is made to U.S. Pat. Nos. 4,474,657, 4,518,471, 4,525,249 and 5,715,133, each of which is incorporated herein by reference, for a description of increasing the surface area of the foil by electrochemically removing portions of the foil to create etch tunnels, applicable to the invention described herein. Since the capacitance of an electrolytic capacitor increases with the surface area of its electrodes, increasing the surface area of the anode foil results in increased capacitance per unit volume of the electrolytic capacitor. By electrolytically etching an anode foil, an enlargement of a surface area of the foil will occur. Electrolytic capacitors which are manufactured with such etched foils can obtain a given capacity with a smaller volume than an electrolytic capacitor which utilizes a foil with an unetched surface. In a preferred embodiment, the aluminum foil is etched in a high temperature etch electrolyte that is based on a halide and/or oxyhalide, preferably a chloride and/or oxychloride, and contains an oxidizer or oxidizing agent such as peroxide, persulfate, cerium sulfate or sodium periodate, at a pH of 0.0 to 8.0, preferably a pH of 1.0 to 3.0. Other surface area enhancing etch solutions can be used with the present invention to produce similar results. In the preferred embodiment, the electrolyte etch solution consists of 0.1% to 10% NaCl, preferably 1.3% NaCl, and 0.1% to 10% $NaClO_4$, preferably 3.5% $NaClO_4$. In some embodiments, the electrolyte etch solution is a low pH etch solution. Reference is made to U.S. Pat. No. 6,858,126, incorporated herein by reference, for a description of low pH etch solutions for producing an etched foil for a capacitor applicable to the invention described herein. The electrolyte is heated to a temperature of 80° C. to 100° C., with a preferred temperature of 85° C. The foil is placed in the etch electrolyte and etched at a current density of 0.1 to 0.3 amps/cm$^2$, preferably 0.15 amps/cm$^2$, and at an etch charge of 5 to 50 Coulombs/cm$^2$ for a specific amount of time, preferably 36 Coulombs/cm$^2$ for 4 minutes.

The pattern is configured in such a way that the enhanced area does not create large scale strength defects such as perforation holes, divots, chunk removal and the like, and can be applied in any size or shape desired, such as round, square, hexagonal, triangular, or any other shape, that will produce the desired results of the present invention. The mask may also be applied in strength line patterns. The strength lines may be in any pattern, including parallel or intersecting lines. The preferred pattern according to the present invention is one that allows the capacitance gain to be enhanced, while the strength is maintained. The mask and pattern are chosen to optimize the etch area as compared to the masked area to achieve the full benefit of the present invention.

Next, the foil may be rinsed in an overflow deionized water bath for a time of 1 to 10 minutes, preferably 1.5 minutes.

After the etching step, the etch-resistant mask is removed using chemical means or treatment in an oven to burn the etch-resistant mask away. The specific conditions to remove the etch-resistant mask can be any suitable conditions to remove the mask without damaging the anode foil. In embodiments where the mask comprises acrylic ink, the mask may be removed using ethyl lactate. In some embodiments, the mask is removed using chemical means, using a solvent that does not react with aluminum or aluminum oxide under the conditions used.

The foil is then widened in a chloride or nitrate containing electrolyte solution known to those skilled in the art, such as that disclosed in U.S. Pat. Nos. 3,779,877 and 4,525,249.

Figure 1A:
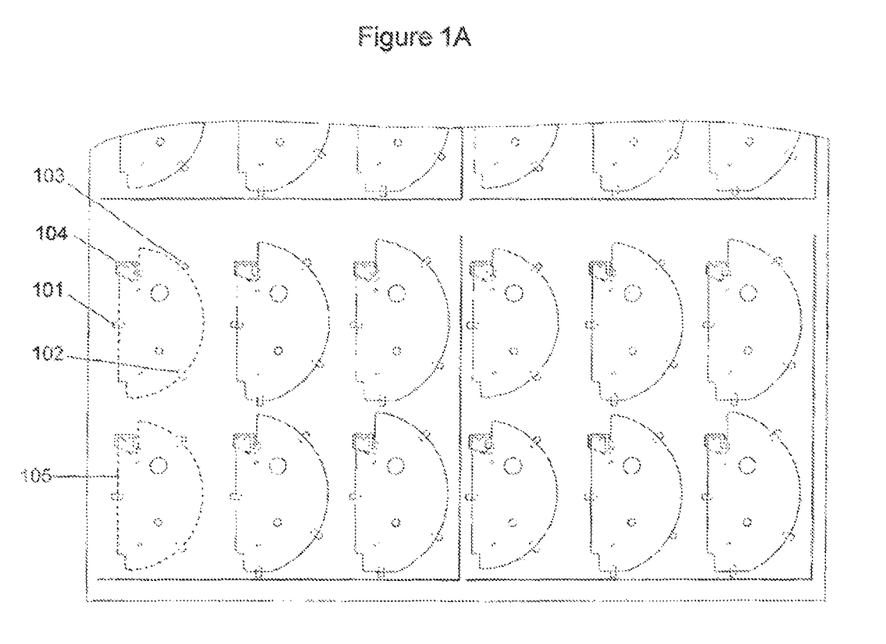
FIGS. 1A and 1B show a schematic depicting masked tab areas relative to unmasked areas to be etched according to the present disclosure.
Figure 1B:
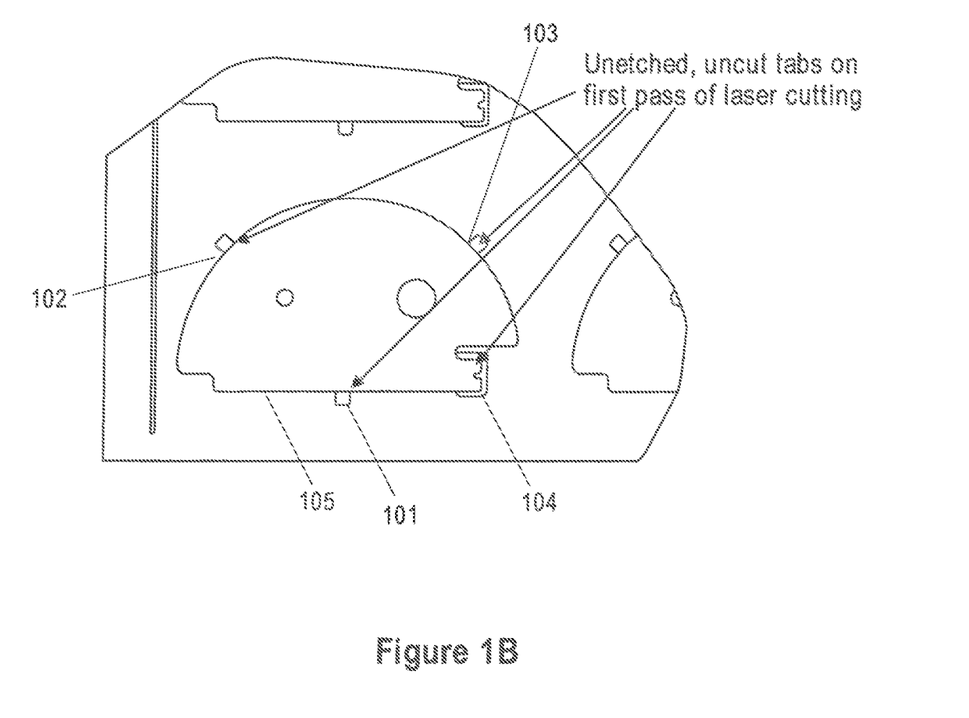

Next, the anodes are partially cut out like in FIG. 1, but the present disclosure is not limited to this example. The foil is partially cut between tabs such that the unetched tabs are not cut and keep the partially detached etched foil anode attached to the bulk metal foil. In some embodiments, the metal foil is partially cut under an inert atmosphere. Cuts can be made between unetched areas to form certain geometries of an anode foil. In some embodiments, the unetched areas are contained partially within the partially detached etched foil anode and partially within the bulk metal foil. In some embodiments, the etched area of the partially detached etched foil anode is greater than the sum of the unetched areas of the partially detached etched foil anode. In some embodiments, one of the plurality of unetched area of the partially detached etched foil anode is larger than the remaining plurality of unetched areas of the partially detached etched foil anode. In some embodiments, the etched area of the partially detached etched foil anode forms a majority of the area of the partially detached etched foil anode. For example, in some embodiments, the etched area forms greater than 50% of the area of the partially detached etched foil anode. In some embodiments, the etched area forms 51-99%, 51-91%, 51-83%, 51-75%, 51-67%, 51-59%, 59-99%, 59-91%, 59-83%, 59-75%, 59-67%, 67-99%, 67-91%, 67-83%, 67-75%, 75-99%, 75-91%, 75-83%, 83-99%, 83-91%, or 91-99% of the area of the partially detached etched foil anode. In some embodiments, the etched area forms 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the area of the partially detached etched foil anode.

Then the foil is dipped into a deionized water bath at a temperature of about 80° C. to about 100° C., preferably about 95° C. to form a hydrate later on the foil surface. Alternatively, the foil is put through a chemical dip or electrochemical process to clean the edges before hydration. The preferred cleaning process is a cleaning step that employs the same solution as the widening step and lasts only 1-10 seconds, followed by a sonic vibration rinse. This process will also remove any alpha-corundum oxide. The sonic vibration rinse can be used to clean the anode foils further. According to an embodiment, the anode foils are cleaned of the widening solution using sonic vibration after the cleaning step. The anode foils may be sonicated in a fluid (e.g., deionized water) at lower frequencies than those normally used in an ultrasonic bath. For example, the anode foils are sonicated at a frequency between 50 Hz and 1 kHz, preferably at a frequency below 300 Hz, or below 100 Hz. The foils may be sonicated in other fluids other than deionized water, so long as the fluid does not damage or leave any residue behind on the anode foils. The increased rinsing energy from the vibrations allows a significantly improved rinse of the widening solution and aluminum for removal in the tunnels. The low frequencies are sufficiently energetic to clean out the tunnels, while being insufficiently energetic to damage the desirable microscopic features of the tunnel structures formed in prior processing of the anode foils. The hydraulic waves create differential pressure on the face of etched anode foils being washed within the bath which compel microscopic particles and residual chemistry from prior process steps out of the microscopic tunnels contained therein.

One reason for using lower frequencies is that higher (e.g., ultrasonic) frequencies would hydrate the foil. This hydration coupled with the vibrational energy being applied can cause pieces of the foil to break off exposing a fresh aluminum surface to be hydrated. This process may continue until the foil dissolves.

Numerous benefits are realized when using the sonicating rinse to remove the widening solution and other impurities vs. a cascading rinse. For example, foil capacitance is increased when using the sonicating rinse to remove the widening solution. In one particular example, foil capacitance is increased by about 4% when using the sonicating rinse as compared to the cascading rinse to remove the widening solution. Additional benefits include increased porosity and therefore, an improved delivered to stored ratio (DSR) thus improving charging time of the capacitors. Also, less surface erosion on the foil surface improves the anode strength leading to higher anode punch yields. Because of the increased efficiency of the sonic vibrational energy, the sonic rinsing system reduces the necessary rinse process time from around 30 minutes to around 5 minutes.

Next, a barrier oxide layer may be electrochemically fully formed onto one or both surfaces of the metal foil, sufficiently thick to support the intended use voltage, by placing the foil into a forming solution, including but not restricted to a solution based on azelaic acid, sebacic acid, suberic acid, adipic acid, dodecanedioic acid, citric acid or other related organic acids and salts, preferably a citric acid solution at a temperature of 80° C. to 100° C., preferably 85° C., at a current density of 1 mA/cm$^2$ to 40 mA/cm$^2$, preferably 16 mA/cm$^2$. A formation voltage of 50 to 800 Volts, preferably 490 V, can be applied to the foil to form the barrier oxide layer. The barrier oxide layer provides a high resistance to current passing between the electrolyte and the metal foils, also referred to as the leakage current. A high leakage current can result in the poor performance and reliability of an electrolytic capacitor. In particular, a high leakage current results in greater amount of charge leaking out of the capacitor once it has been charged. In some embodiments, the metal foil is formed before the partial cutting step.

A heat treatment of 500° C.±20° C. may be applied to the foil following formation for 1 to 10 minutes, preferably 4 minutes. The foil is then returned to the forming solution and allowed to soak with no applied potential for 1 to 10 minutes, preferably 2 minutes. A second formation in the same electrolytic forming solution at high temperature is performed at a potential of 480 Volts.

Next, the foils are dipped in a suitable low concentration oxide-dissolving acid solution for passivation. Suitable acids include but are not restricted to phosphoric acid, formic acid, acetic acid, citric acid, and oxalic acid, preferably phosphoric acid, a concentration of 1% to 10%, preferably a concentration of 2%, at a temperature of 60° C. to 90° C., preferably 70° C., for an time of 1 to 10 minutes, preferably 4 minutes.

Next, the foils are reformed at a voltage of 480 Volts in a suitable forming solution, as discussed above, at a high temperature, preferably 80° C. to 100° C., more preferably 85° C.

Finally, the foil is finally cut through the unetched tabs, to form a cut etched foil anode, detaching or removing it from the bulk metal foil. The foil is finally cut such that the unetched tab areas are partially contained within the cut etched foil anode perimeter and partially contained within the remainder of the bulk metal foil. The conditions for cutting the anode foils can be any suitable conditions known to persons of skill in the art. In some embodiments, the foil is laser cut. Suitable conditions are those which achieve an ablative threshold for the material and then limit the heat input and provide a good atmosphere for the nascent surfaces and finishing off with debris removal. In some embodiments, it is desirable to maintain as low an energy as possible to cut the foil while minimizing the heating effect. In some embodiments, the cleaning step is after formation and laser cutting. In some embodiments, the foil is laser cut using a number of passes through the foil to cut the foil. In some embodiments, the number of passes necessary to finally cut the etched foil anode is reduced compared to that necessary for an etched foil anode cut without partial cutting. For example, in some embodiments, the number of passes is reduced by about 5%, about 10%, about 15%, about 20%, about 25, or about 30% compared to that necessary for an etched foil cut without partial cutting.

In some embodiments, the cut etched foil anode has over 80% of the edge formed. For example, in some embodiments, the cut etched foil anode has 80-100%, 80-96%, 80-92%, 80-88%, 80-84%, 84-100%, 84-96%, 84-92%, 84-88%, 88-100%, 88-96%, 88-92%, 92-100%, 92-96%, or 96-100% of the edge formed. In some embodiments, the cut etched foil anode has 80, 81, 82, 83, 84, 85, 86, 87, 88, 89, 90, 91, 92, 93, 94, 95, 96, 97, 98, 99, or 100% of the edge formed.

Anode foils etched according to the present invention have less thermal oxide formation in the unetched areas and/or along the unetched frame or perimeter than foils cut without a masking step. Thermal oxidation in the anode foils of the present invention is reduced. In certain embodiments, thermal oxidation is reduced by greater than 90%, or by greater than 92%, or by greater than 95%, or by greater than 97%, or by greater than 98%, or by greater than 99%. Anode foils etched according to the present invention will also have enhanced capacitance without the increased brittleness, which would render such foil unusable, typical of anode foils highly etched according to conventional methods. Foils that are processed according to the present invention can be utilized for a variety of applications that require a high capacitance foil. For example, as discussed above, high capacitance anode foils are widely utilized in electrolytic capacitors. Electrolytic capacitors comprising anode foils manufactured according to the present invention exhibit improved leakage current compared to capacitors manufactured with anode foils etched by a process not using a partial cutting step. In some embodiments, the leakage current is improved by about 20-30%. Electrolytic capacitors, which are manufactured with anode foils etched according to the present invention, can obtain a given capacity with a smaller volume than currently available electrolytic capacitors and, therefore, can be very compact in size.

Electrolytic capacitors manufactured with anode foils etched according to the present invention can be utilized in ICDs, such as those described in U.S. Pat. No. 5,522,851 to Fayram, incorporated by reference herein in its entirety, such that the improved leakage current of the electrolytic capacitor allows for a reduction in the size of the ICD.

Having now generally described the invention, the same will be more readily understood through reference to the figures which are provided by way of illustration, and are not intended to be limiting of the present invention.

FIGS. 1A and 1B show a schematic depicting masked tab areas relative to unmasked areas to be etched. FIG. 1A depicts a sheet of metal foil and demonstrates one pattern of masking tabs of anode foils on a bulk metal foil relative to the perimeters of the eventual cut anode foils. Small tabs 101, 102, and 103 as well as large tab 104 are masked as described above. FIG. 1B shows a close up view of a single anode foil, outlining the perimeter 105 and tab areas, small tabs 101, 102 and 103, and large tab 104. The tabs are labeled as being unetched and uncut on the first pass of laser cutting.

Figure 2A:
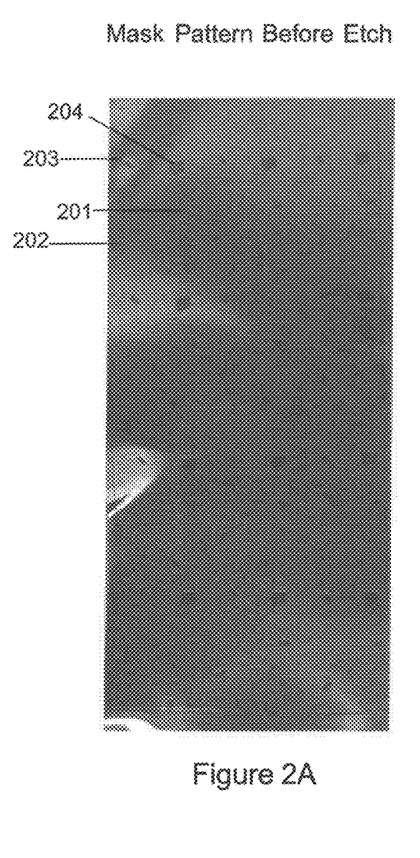
FIGS. 2A and 2B show photographs of a masked tab pattern on a bulk metal foil according to the present disclosure.
Figure 2B:
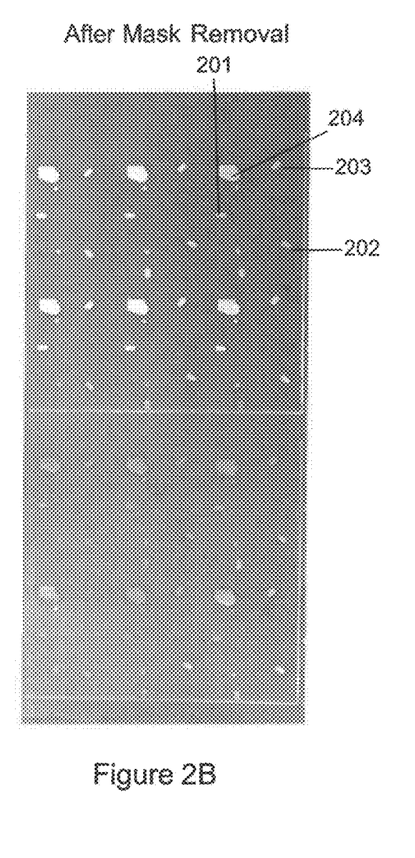

FIGS. 2A and 2B are photographs of a masked tab pattern on a bulk metal foil. The photograph on the left (FIG. 2A) shows the mask pattern before etching, with small tabs 201, 202, and 203 and large tab 204 masked as described above. FIG. 2B shows the same foil after etching and mask removal.

Figure 3:
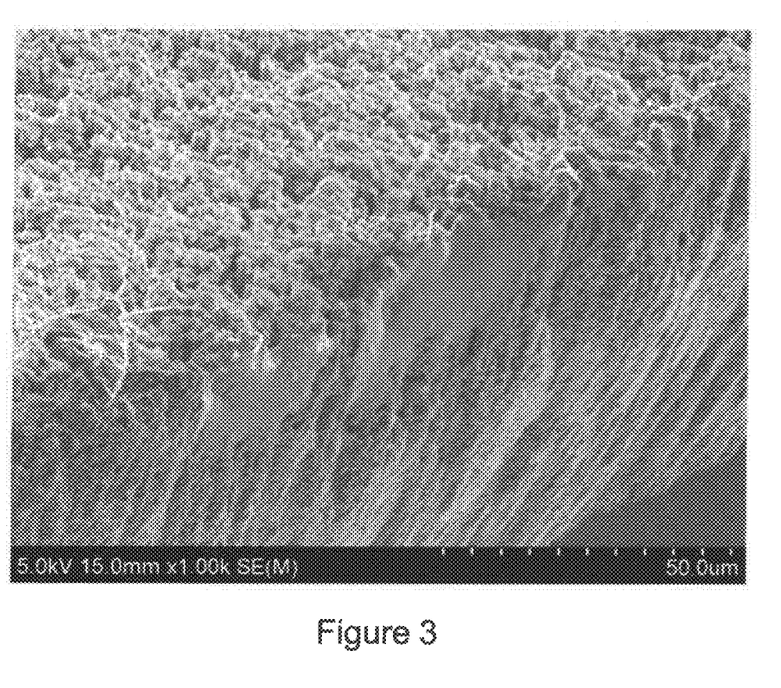
FIG. 3 shows an SEM photograph of a foil anode edge after the final laser cutting that occurs after formation.

FIG. 3 shows an SEM photograph after the partial laser cutting that occurs after formation. The alpha-phase corundum is visibly present.

Figure 4A:
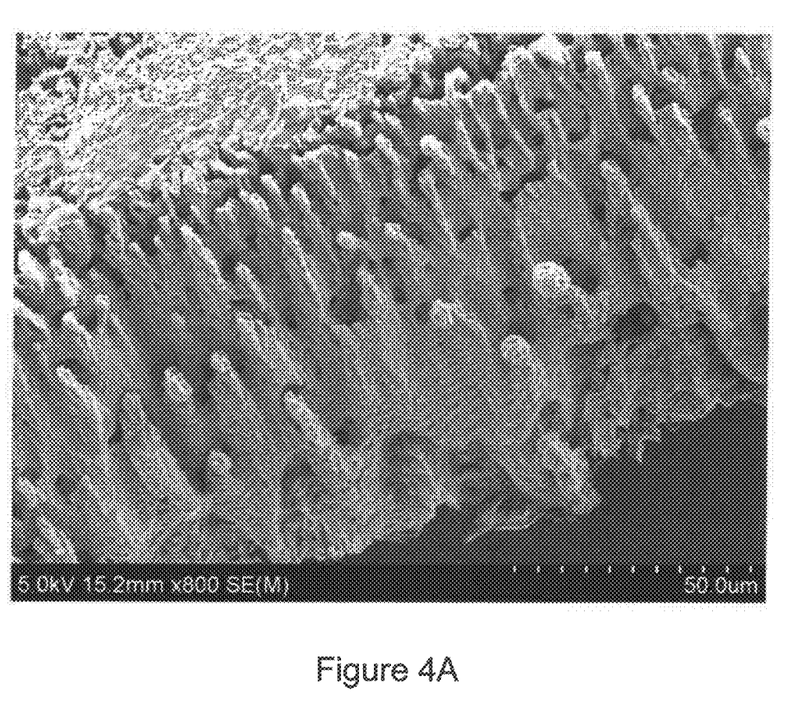
FIGS. 4A and 4B show two SEM photographs of an anode edge that has been laser cut after etching and widening, and before formation.
Figure 4B:
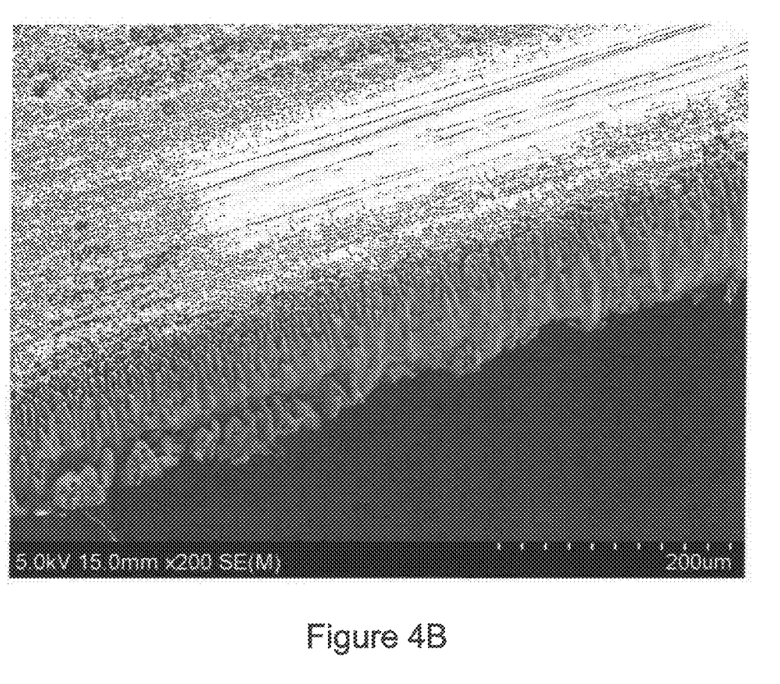
Figure 5:
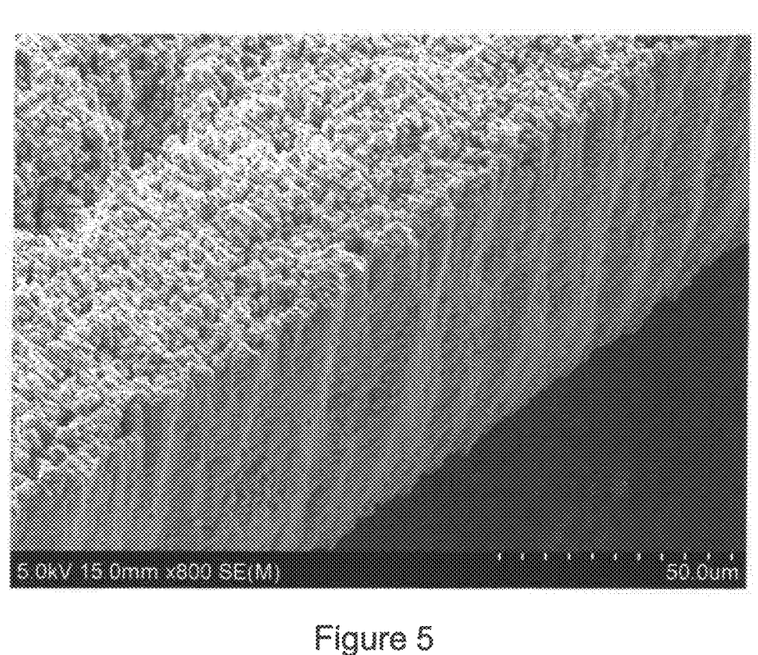
FIG. 5 shows an SEM photograph of the same anode edge of FIGS. 4A and 4B after formation.

FIG. 4A and FIG. 4B show two SEM photographs of an anode edge that has been partially laser cut after etching and widening, and before formation. FIG. 5 shows an anode edge after formation of the edge presented in FIGS. 4A and 4B. The edge in FIG. 5 looks smooth, without the alpha phase corundum on the edge, as it has been mostly converted to a high quality boehmite oxide.

Figure 6:
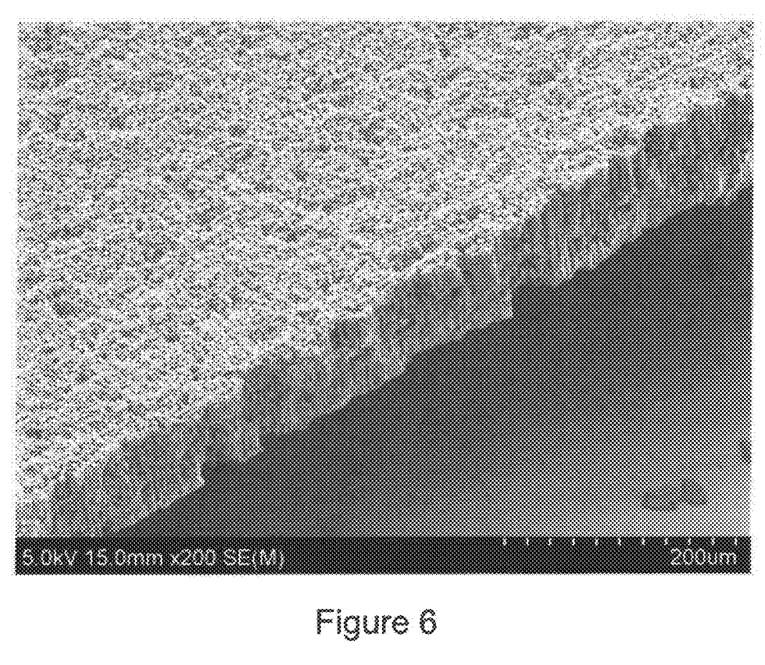
FIG. 6 shows an SEM photograph of an anode edge after formation, final laser cutting, and cleaning.

FIG. 6 shows an SEM photograph of an anode edge after formation, final laser cutting, and cleaning with an electrochemical widening process. The anode edge is completely clean of the alpha phase corundum oxide.

Figure 7:
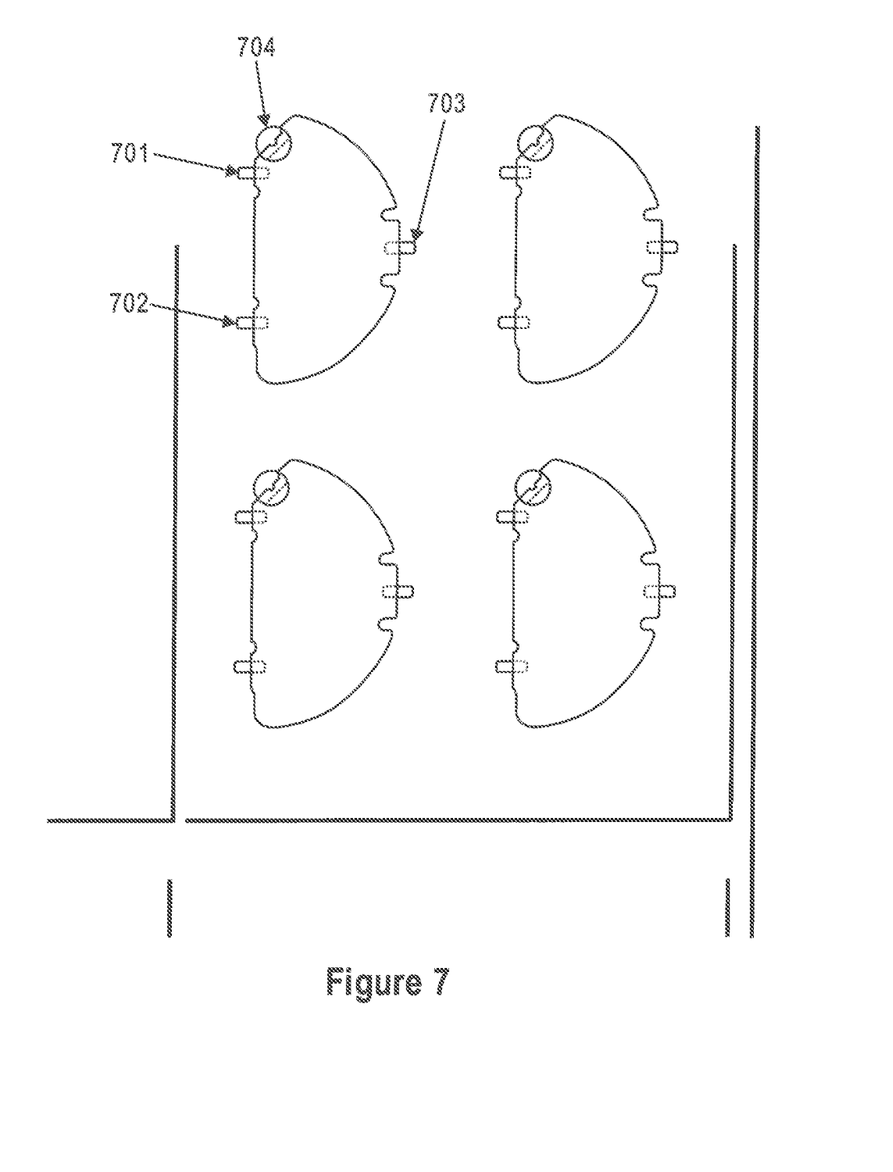
FIG. 7 shows a schematic depicting masked tab areas relative to unmasked areas to be etched according to the present disclosure.

FIG. 7 shows a schematic depicting masked tab areas relative to unmasked areas to be etched, with an alternate geometry of an anode foil compared to FIGS. 1A and 1B. Small tabs 701, 702, and 703, as well as large tab 704 are masked as described above.

Figure 8:
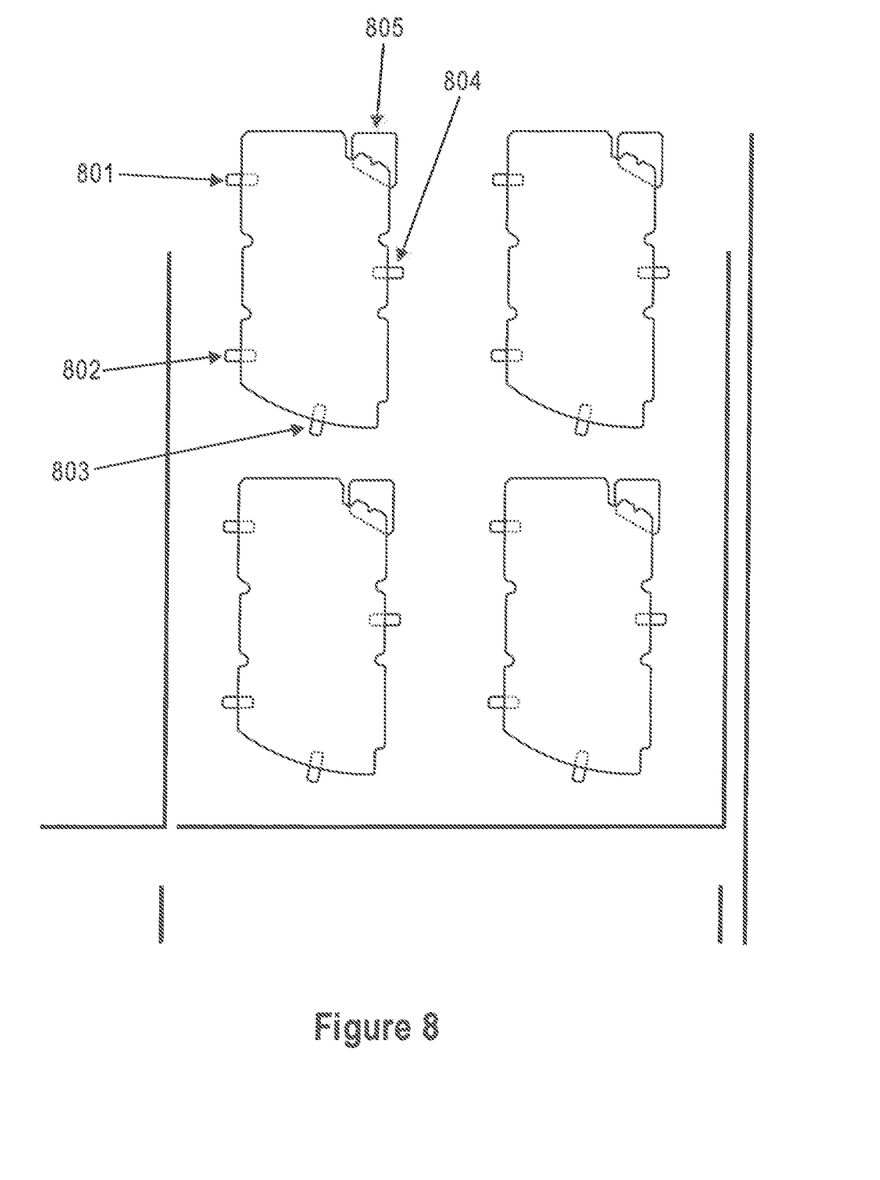
FIG. 8 shows a schematic depicting masked tab areas relative to unmasked areas to be etched according to the present disclosure.

FIG. 8 shows a schematic depicting masked tab areas relative to unmasked areas to be etched, with an alternate geometry of an anode foil compared to FIGS. 1A, 1B, and 7. Small tabs 801, 802, 803, and 804, as well as large tab 805 are masked as described above.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A process of etching a metal foil, comprising:
    applying an etch-resistant mask to predetermined portions of a bulk metal foil to define a plurality of masked areas;
    placing the partially masked bulk metal foil in an etch electrolyte solution to etch the exposed area of the bulk metal foil;
    removing the etch-resistant mask to expose the unetched areas;
    widening the bulk metal foil; and
    partially cutting the bulk metal foil between a plurality of unetched areas to form a partially detached etched foil anode, such that the unetched areas are not cut and the unetched areas serve as attachment tabs to keep the partially detached etched foil anode attached to the bulk metal foil.

2. The process of claim 1, further comprising the step of forming a barrier oxide layer onto at least one surface of the bulk metal foil before partially cutting the bulk metal foil and after widening the bulk metal foil.

3. The process of claim 1, wherein one of the plurality of unetched areas of the partially detached etched foil anode is larger than the remaining plurality of unetched areas of the partially detached etched foil anode.

4. The process of claim 1, wherein the etched area of the partially detached etched foil anode forms a majority of the area of the partially detached etched foil anode.

5. The process of claim 1, further comprising:
    finally cutting the partially detached etched foil anode, to form a cut etched foil anode having a perimeter, wherein finally cutting comprises removing the partially detached etched foil anode from the bulk metal foil,
    such that the unetched areas are partially contained within the cut etched foil anode perimeter and partially contained within a remainder of the bulk metal foil.

6. The process of claim 1, wherein the metal foil is aluminum foil.

7. The process of claim 1, wherein the metal foil is partially cut under an inert atmosphere.

8. The process of claim 1, further comprising:
    hydrating the partially detached etched foil anode;
    forming a barrier oxide layer onto at least one surface of the partially detached etched foil anode; and
    finally cutting the partially detached etched foil anode, to form a cut etched foil anode having a perimeter, wherein finally cutting comprises removing the partially detached etched foil anode from the bulk metal foil,
    such that the unetched areas are partially contained within the cut etched foil anode perimeter and partially contained within a reminder of the bulk metal foil.

9. The process of claim 8, further comprising the step of cleaning the partially detached etched foil anode before forming the barrier oxide layer.

10. The process of claim 1, wherein the etch electrolyte solution comprises a sulfate, a halide, and an oxidizing agent, in an aqueous solvent.

11. The process of claim 1, wherein the area defined by the etch-resistant mask defines a set of strength lines, and wherein the etch-resistant mask is applied to one face of the foil.

12. A metal anode foil etched by the process of claim 1.

13. A capacitor comprising the anode foil of claim 12, wherein the capacitor has a leakage current that is improved by about 20-30% compared to the leakage current of a capacitor consisting essentially of one or more anode foils created without partial cutting.

14. A process of creating a metal anode foil, comprising:
applying an etch-resistant mask to predetermined portions of a bulk metal foil to define a plurality of masked areas;
placing the partially masked bulk metal foil in an etch electrolyte solution to etch the exposed area of the bulk metal foil, and etching said masked bulk metal foil, such that the exposed area is etched;
removing the etch-resistant mask to expose the unetched areas;
widening the bulk metal foil;
partially cutting the bulk metal foil between a plurality of unetched areas to form a partially detached etched foil anode, such that the unetched areas are not cut and the unetched areas serve as attachment tabs to keep the partially detached etched foil anode attached to the bulk metal foil,
hydrating the partially detached etched foil anode;
forming a barrier oxide layer onto at least one surface of the partially detached etched foil anode; and
finally cutting the partially detached etched foil anode, to form a cut etched foil anode having a perimeter and an edge, wherein finally cutting comprises removing the partially detached etched foil anode from the bulk metal foil, such that the unetched areas are partially contained within the cut etched foil anode perimeter and partially contained within a remainder of the bulk metal foil,
and wherein the cut etched foil anode has over 80% of the edge formed.

15. The process of claim 14, further comprising the step of forming the barrier oxide layer onto the at least one surface of the bulk metal foil before partially cutting the bulk metal foil and after widening the bulk metal foil.

16. The process of claim 14, wherein the mask is applied to both faces of the foil.

17. The process of claim 14, wherein the mask is applied to one face of the foil.

18. The process of claim 17, wherein the area defined by the mask defines a set of strength lines.

19. The process of claim 14, wherein the metal foil is an aluminum foil.

20. The process of claim 14, wherein the etch-resistant mask is selected from the group consisting of an acrylic ink, poly(4-hydroxystyrene), copolymers of 4-hydroxystyrene, novolac resins, fluorocarbon polymers, cycloaliphatic polymers, polyurethane polyols, polyesterurethanes, and cross-linked variants and copolymers and mixtures thereof.

21. The process of claim 14, wherein said applying the etch-resistant mask to predetermined portions of the foil is performed to provide a plurality of masked areas that define a perimeter when the foil is cut between the masked areas.

* * * * *